United States Patent [19]

Muir

[11] 4,402,976
[45] Sep. 6, 1983

[54] METHOD FOR TREATING GLAUCOMA WITH SYSTEMIC NADOLOL COMPOSITIONS

[75] Inventor: John G. Muir, Pennington, N.J.

[73] Assignee: E. R. Squibb & Sons, Inc., Princeton, N.J.

[21] Appl. No.: 257,453

[22] Filed: Apr. 24, 1981

[51] Int. Cl.³ .................... A61K 31/22; A61K 31/135
[52] U.S. Cl. ...................................... 424/311; 424/330
[58] Field of Search ................................ 424/311, 330

[56] References Cited

U.S. PATENT DOCUMENTS

| | | | |
|---|---|---|---|
| 3,935,267 | 1/1976 | Hauck et al. | 424/330 |
| 3,982,021 | 9/1976 | Hauck et al. | 424/330 |
| 4,029,676 | 6/1977 | Hauck et al. | 424/311 |
| 4,275,074 | 6/1981 | Langham | 424/311 |
| 4,346,106 | 8/1982 | Sudilovsky | 424/311 |

FOREIGN PATENT DOCUMENTS 1524405 9/1976 United Kingdom .
1559987 11/1976 United Kingdom .

OTHER PUBLICATIONS

Batchelor et al., "Interaction of Topical and Oral Timolol in Glaucoma" Ophthamology, 86:60–65, 1979.
Coté et al., "The Effect of Propranolol on Human Intraocular Pressure" Canad. J. Ophthal., 3:207, 1968.
Wettrell et al., "Beta–Adrenoceptor Blocking Agents in the Management of Glaucoma" Bellows Glaucoma Contemporary International Concepts, Chapter 23, pp. 367–375.

Primary Examiner—Douglas W. Robinson
Attorney, Agent, or Firm—Lawrence S. Levinson; Burton Rodney

[57] ABSTRACT

A method is provided for treating glaucoma by systemic administration of nadolol or esters of nadolol.

8 Claims, No Drawings

METHOD FOR TREATING GLAUCOMA WITH SYSTEMIC NADOLOL COMPOSITIONS

FIELD OF THE INVENTION

The present invention relates to a method for treating glaucoma and/or of lowering intraocular pressure by systemically administering nadolol or an ester thereof.

BACKGROUND OF THE INVENTION

British patent specification No. 1,524,405 discloses the use of timolol (S-(−)-1-(t-butylamino)-3-[(4-morpholino-1,2,5-thiadiazol-3-yl)oxy]-2-propanol

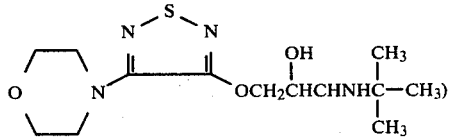

for treating glaucoma by topically administering same to the eye.

Batchelor et al, "Interaction of Topical and Oral Timolol in Glaucoma," Ophthamology, 86:60–65, 1979, disclose that both oral and topical preparations given separately produce a significant and comparable reduction of intraocular pressure.

Coté et al, "The Effect of Propranolol on Human Intraocular Pressure," Canad. J. Ophthal. 3:207, 1968 disclose that propranolol (1-(isopropylamino)-3-(1-naphthyloxy)-2-propanol

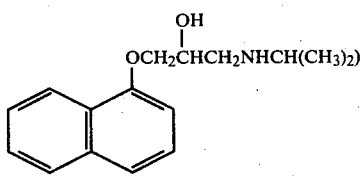

administered orally (20 mg to 50 mg/day/2–7 months) was helpful in reducing intraocular pressure of some patients, especially when the patients could not tolerate or were not well controlled by other medical glaucoma therapy.

Wettrell et al, "Beta-Adrenoceptor Blocking Agents in the Management of Glaucoma," Bellows Glaucoma Contemporary International Concepts, Chapter 23, pp. 367–375 disclose that atenolol

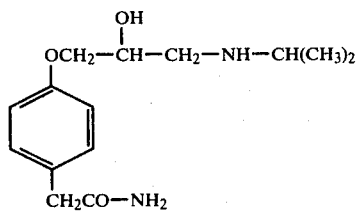

and propranolol are orally active in treating glaucoma.

DESCRIPTION OF THE INVENTION

In accordance with the present invention, a method is provided for treating glaucoma and/or of lowering intraocular pressure in mammalian species wherein a therapeutically effective amount of nadolol or an ester thereof is systemically, preferably orally, administered.

The term "nadolol" as employed herein refers to the beta blocker 2,3-cis-1,2,3,4-tetrahydro-5-[2-hydroxy-3-(tert-butylamino)propoxy]-2,3-naphthalenediol (and pharmaceutically acceptable acid-addition salts thereof)

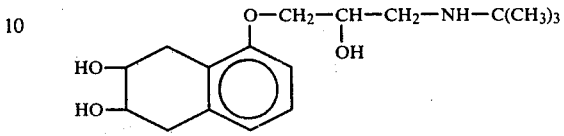

which is disclosed in U.S. Pat. Nos. 3,935,267 and 3,982,021, the aforementioned patents being incorporated herein by reference.

Esters of nadolol included herein are the mono-, di- and tri-esters (and pharmaceutically acceptable acid-addition salts thereof).

The di-esters have the structure

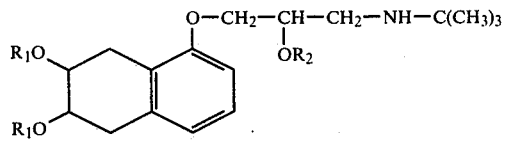

wherein both $R_1$ groups are acyl, preferably acetyl, and $R_2$ is hydrogen, are disclosed in U.S. Pat. No. 4,029,676 which is incorporated herein by reference.

Esters of nadolol wherein both $R_1$ groups are hydrogen and $R_2$ is acyl (mono-ester), preferably acetyl, and wherein both $R_1$ groups are acyl, preferably acetyl, and $R_2$ is acyl, preferably acetyl (tri-esters) are disclosed in British patent specification No. 1,559,987 which is incorporated herein by reference.

In carrying out the method of the present invention, the nadolol or nadolol ester or a physiologically acceptable acid-addition salt may be administered to mammalian species, such as monkeys, dogs, cats, rats, etc. and as such may be incorporated in a conventional dosage form, such as a tablet, capsule, elixir, injectable or the like along with the necessary carrier material, excipient, lubricant, buffer, or the like. Oral dosage forms are preferred, although parenteral forms are quite satisfactory as well. Single or divided doses of about 8 to about 120 mg, preferably about 20 to 80 mg/one to four times daily may be administered in dosage forms as described above.

The following working Example represents a preferred embodiment hereof.

EXAMPLE

A nadolol formulation suitable for oral administration in the treatment of glaucoma is set out below.

| Ingredient | mg/tablet |
| --- | --- |
| Nadolol | 40 |
| Magnesium stearate | 1 |
| Microcrystalline cellulose | 72 |

The nadolol is blended with the microcrystalline cellulose in a Hobart-type mixer for 5 minutes. Thereafter, the magnesium stearate is added with mixing for 2–3 minutes. The final mix is compressed in a Strokes D3 tablet press to form a 40 mg tablet which is used for treating glaucoma or reducing intraocular pressure.

What is claimed is:

1. A method for treating glaucoma or lowering intraocular pressure in a mammalian species, which comprises systemically administering once a day an effective amount of nadolol or an ester thereof or a pharmaceutically acceptable acid-addition salt of said nadolol or ester thereof.

2. The method as defined in claim 1 wherein said nadolol or ester thereof is administered orally.

3. The method as defined in claim 1 wherein said ester is a mono-, di- or tri-ester.

4. The method as defined in claim 3 wherein said ester is a monoacetate, diacetate or triacetate.

5. The method as defined in claim 1 wherein said nadolol or ester thereof is admixed with a pharmaceutically acceptable carrier therefor.

6. The method as defined in claim 1 wherein said nadolol or ester thereof is administered in a dosage of from about 8 to about 120 mg.

7. The method as defined in claim 6 wherein said nadolol or ester thereof is administered in a dosage of from about 20 to about 80 mg.

8. The method as defined in claim 1 wherein said nadolol or ester thereof is in the form of a pharmaceutically acceptable acid-addition salt thereof.

* * * * *